United States Patent
Betts et al.

[11] Patent Number: 5,777,202
[45] Date of Patent: Jul. 7, 1998

[54] REFERENCE SOLUTION CONTAINER HAVING IMPROVED GAS RETENTION

[75] Inventors: Ronald E. Betts, La Jolla; Douglas R. Savage, Del Mar; Michael C. Weinzierl, San Diego, all of Calif.

[73] Assignee: SenDx Medical, Inc., Carlsbad, Calif.

[21] Appl. No.: 690,042

[22] Filed: Jul. 31, 1996

Related U.S. Application Data

[63] Continuation-in-part of Ser. No. 650,465, May 20, 1996.

[51] Int. Cl.⁶ .................................................. G01N 33/49
[52] U.S. Cl. .................................................. 73/1.03; 73/1.05
[58] Field of Search ....................... 73/1.03, 1.04, 73/1.05; 204/401, 427, 428, 429

[56] References Cited

U.S. PATENT DOCUMENTS

| | | | |
|---|---|---|---|
| 3,874,850 | 4/1975 | Sorensen et al. | 356/40 X |
| 4,003,705 | 1/1977 | Buzza et al. | |
| 4,116,336 | 9/1978 | Sorensen et al. | 206/524.8 |
| 4,649,028 | 3/1987 | Kaltenbach et al. | 422/100 |
| 4,753,888 | 6/1988 | Chiang | 436/11 |
| 4,871,439 | 10/1989 | Enzer et al. | 204/401 |
| 5,023,186 | 6/1991 | Herring | 436/11 |
| 5,134,875 | 8/1992 | Jensen et al. | 73/1.03 |
| 5,230,427 | 7/1993 | Betts et al. | 206/213.1 |
| 5,284,570 | 2/1994 | Savage et al. | 204/409 X |
| 5,405,510 | 4/1995 | Betts et al. | 204/409 X |

FOREIGN PATENT DOCUMENTS

2 100 859  1/1983  United Kingdom.

*Primary Examiner*—Thomas P. Noland
*Attorney, Agent, or Firm*—Fish & Richardson P.C.

[57] ABSTRACT

A reference solution container for an analyzer for measuring gas and/or electrolyte levels in a fluid. The vessel includes a fluid container for holding a reference solution and a self-sealing fluid port for repeatedly accessing the reference solution in the fluid vessel by a fluid carrying device that is external to the reference solution container. The partial pressure of each gas in the reference solution within the fluid vessel is maintained at a substantially constant level.

12 Claims, 7 Drawing Sheets

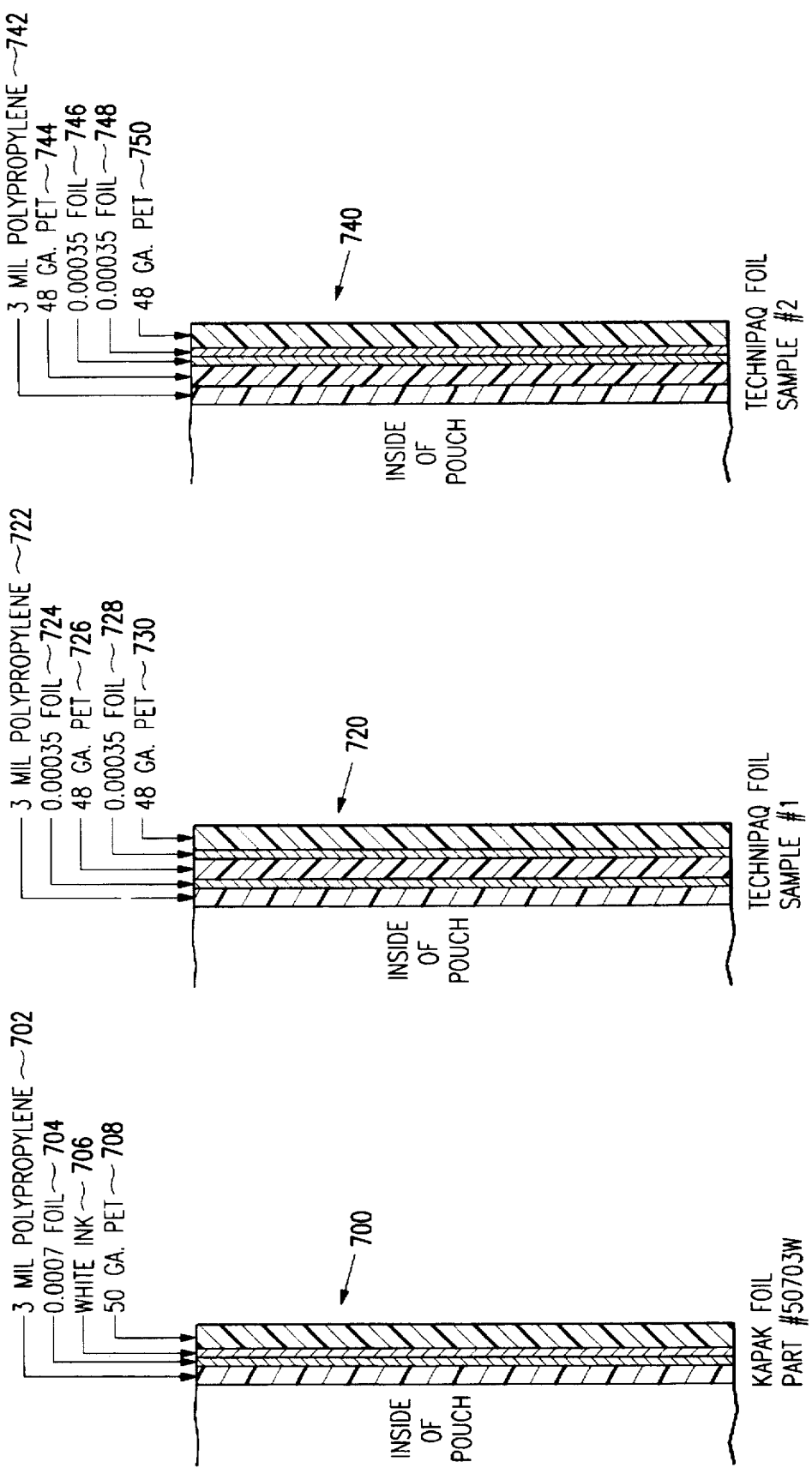

REFERENCE SOLUTION CONTAINER HAVING IMPROVED GAS RETENTION

RELATED APPLICATIONS

This application is a continuation-in-part of U.S. patent application Ser. No. 08/650,465, filed May 20, 1996, entitled "Reference Solution Container for Blood Gas/Electrolyte Measuring System", now pending.

BACKGROUND OF THE INVENTION

1. Field of the Invention

The present invention relates to a reference solution container for a fluid analysis device. More particularly, the present invention relates to a container for a reference or calibration solution, where the container has improved gas retention characteristics, such that gases in the solution at a known partial pressure are maintained at or near that pressure during storage and use.

2. Description of Related Art

Various fluid analysis devices are used in testing and measuring gas and/or electrolyte levels in fluids. These devices are used, for example, in medical and environmental applications to measure the gas and/or electrolyte levels in blood, urine, water, and other fluids.

Fluid analysis devices must be calibrated frequently when they are being used to test fluid samples. For example, it is preferable to recalibrate a blood analyzer after each blood sample is tested for gas and/or electrolyte levels. As a result, it is essential to provide some means of applying a reference or calibration solution to the fluid analysis devices. In many cases, a reference or calibration solution container can be coupled to the fluid analysis machine, thereby providing a ready means of recalibrating the fluid analysis machine when testing samples.

A reference or calibration container holds a reference or calibration solution that contains gases, such as oxygen and carbon dioxide, in solution at known partial pressures. Because these partial pressures are known to a relatively precise degree, the reference or calibration solution can be used to accurately calibrate the fluid analysis machine after fluid samples have been tested. Yet, such containers are frequently stored for weeks or months and are also frequently left attached to the fluid analysis machine for several weeks before they are completely depleted of reference or calibration solution and are replaced with a new container. Thus, a reference or calibration solution container must be designed such that it can reliably maintain the partial pressures of the gases in solution while the container is stored and/or attached to a fluid analysis machine.

Conventional containers employ a multi-layer laminate, where the interior layer of the container contacting the solution is polyethylene and the exterior is aluminum foil. This combination has proven effective in maintaining the partial pressure of oxygen gas in solution for relatively short periods of storage and use. It is desirable, however, to increase the duration for which the container can substantially maintain the oxygen partial pressure level at a known initial level. Such an increased duration means that the container will have a greater shelf-life and use-life. This provides economies and improves reliability.

Accordingly, a need exists for a reference or calibration solution container that substantially maintains the partial pressure of oxygen gas in solution for a longer period of time than conventional containers. The present invention provides such a container.

SUMMARY OF THE INVENTION

The present invention is a reference or calibration solution container for a fluid analysis device, such as a blood analyzer. The container of the present invention can be used in a variety of applications in which a fluid analyzer must be recalibrated after performing tests on a fluid sample. The container of the present invention can be used in a variety of medical applications as well as in environmental applications in which fluids are being analyzed for gas and/or electrolyte content. Examples of fluids for which the container can be used include blood, water, urine, spinal fluid, and semen.

For convenience, throughout the remainder of this description, the container of the present invention will be described with reference to blood analysis devices and blood samples. It should be understood, however, that the container is not limited to such applications and has a much broader field of use, at least in the applications and with the exemplary fluids set forth above. Furthermore, for convenience, the container of the present invention will be referred to throughout the remainder of this description as a "reference solution container." It should be recognized, however, that the term "reference solution" is intended to encompass calibration solutions and that the container of the present invention can be used for calibration solutions.

The reference solution container of the present invention can be used in a blood analyzer that measures gas and/or electrolyte levels in blood. The container includes a fluid vessel for holding a reference solution and may also include a self-sealing fluid port for repeatedly accessing the reference solution in the fluid vessel by an external fluid carrying device. The reference solution container substantially maintains a partial pressure of gases (such as oxygen and carbon dioxide) in the reference solution. The external fluid carrying device may be part of the blood analyzer, and the reference solution container can be secured to the blood analyzer, such that the external fluid carrying device engages the self-sealing fluid port for repeated access to the reference solution by the blood analyzer. The container may be incorporated into a calibration cartridge that can be secured to the blood analyzer.

The fluid vessel is preferably flexible. The flexible fluid vessel may include a flexible protective layer (such as foam) covering a substantial portion of the exterior of the fluid vessel.

The flexible fluid vessel is formed from multiple layers of material, such as metallic foil and plastic. The metallic foil layer is preferably aluminum, which is strong, lightweight, durable, and inexpensive. The plastic layer is on the interior of the fluid vessel in contact with the reference solution. Preferably, the plastic layer is polypropylene. Polypropylene material provides enhanced performance over conventional polyethylene in maintaining partial pressure level of oxygen gas in the reference solution. Alternatively, a flexible glass layer may be used as the interior layer. This interior plastic or glass layer provides a barrier between the metallic layer and the reference solution. This barrier prevents the metal from reacting with the reference solution and thereby reducing the partial pressure of oxygen gas in solution.

The details of the preferred embodiment in the present invention are set forth in the accompanying drawings and the description below. Once the details of the invention are known, numerous additional innovations and modifications will become obvious to one skilled in the art.

BRIEF DESCRIPTION OF THE DRAWINGS

FIGS. 7A–7C are cross-sections showing alternative embodiments of multi-layered laminates used to form the walls of a fluid vessel in accordance with the present invention.

DETAILED DESCRIPTION OF THE INVENTION

Throughout this description, the preferred embodiment and examples shown should be considered as exemplars, rather than as limitations on the present invention.

I. Overview

Figure 1:
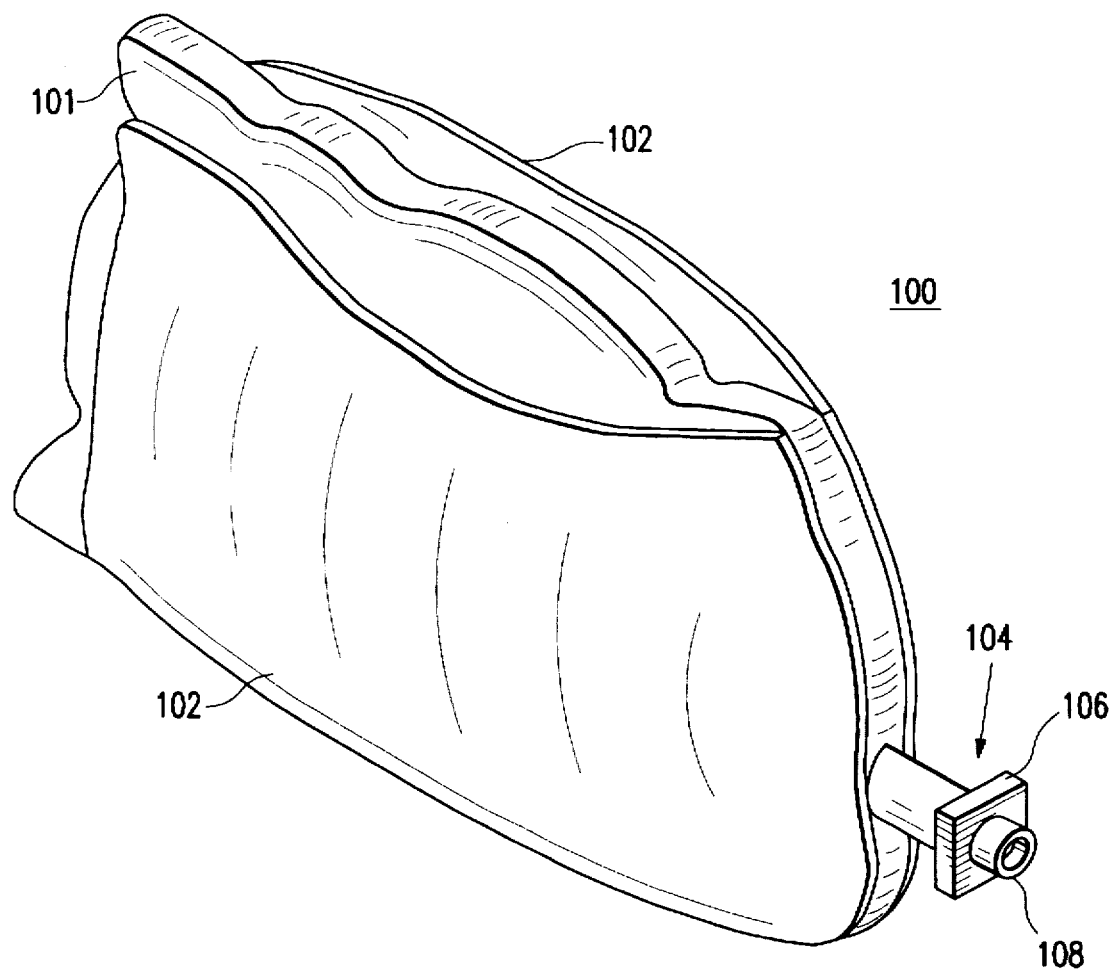
FIG. 1 is a perspective view of a flexible reference solution container of the present invention, in which the container is filled to an internal pressure greater than ambient, and showing a protective layer.

FIG. 1 is a perspective view of a reference solution container 100 in accordance with the present invention. The container 100 holds a reference solution for use in calibrating fluid analysis devices, such as a blood analyzer. The reference solution container 100 has a fluid vessel (or bag) 101 and a self-sealing fluid port 104 for repeatedly accessing the reference solution in the fluid bag 101 by a fluid carrying device (not shown) that is external to the reference solution container. (The fluid vessel 101 will be referred to throughout the remainder of this description primarily as a "fluid bag," because, in the preferred embodiment, the fluid vessel 101 is a flexible, metal-plastic laminate, "bag." It should be understood, however, that the fluid vessel 101 is not intended to be limited to a flexible bag.) The fluid port 104, which will be described in detail below, has a flange 106, a port body 108 for engaging the external fluid carrying device, and a fluid communication port 110. The container 100 may optionally also have a protective layer 102 covering a substantially portion of the exterior of the container 100.

Preferably, the fluid bag 101 is made from a flexible material, preferably an aluminum foil-plastic laminate, and may be filled to an internal pressure that is greater than the ambient atmospheric pressure at sea level surrounding the container 100. (For convenience, a reference solution container that is filled to a greater internal pressure than ambient will be referred to for the remainder of this description as an "over-filled container.") In accordance with this invention, an over-filled container is defined as a reference solution container that is filled to an internal pressure at least about 1.01 times greater than the ambient surrounding pressure at sea level.

The protective layer 102 can be secured to the exterior surface of the fluid bag 101. Preferably, the protective layer is an adhesive-backed foam that is adhered to the fluid bag 101 before it is filled with reference solution. The protective foam 102 may alternatively be applied after the fluid bag 101 is filled. It is desirable to cover substantially all, but not the entirety, of the exterior of the fluid bag 101, in order to maintain a sufficient amount of flexibility in the fluid bag 101 to allow it to contract as it is emptied of reference solution. Either one, two, or more pieces of protective layering (or patches of such layering) can be applied to the container 100, depending on the configuration and size of the fluid bag 101 as well as the desired amount of protection and flexibility of the fluid bag 101.

The protective layer 102 is especially important for an over-filled container. Because such containers are filled to a relatively high internal pressure, they are subject to puncturing from sharp objects and to the formation of pin holes from vibration and motion. The protective layering 102 also facilitates over-filling of the fluid bag 101, because the layering 102 provides additional structural integrity and strength to the (preferably flexible aluminum) fluid bag 101 to reduce the chance of it bursting during filling. It should be understood, however, that the protective layering 102 is not limited to over-filled containers, but rather can be used on any reference solution container for which it is desirable to protect the container from puncturing, tearing, and rupturing. The protective layer 102 has a thickness of at least about 0.005". The protective layer 102, however, may be thicker than 0.005" to provide even greater protection. The layer 102, however, is preferably not so thick that it renders the fluid bag 101 rigid.

The protective layer 102 can alternatively be a protective vinyl (or other suitable) coating. Such a coating is preferably applied by submerging the fluid bag 101 in the coating while it is in a liquid state. When the fluid bag 101 is removed, the coating then dries and forms a protective layer on the fluid bag 101. The coating could optionally be sprayed in a liquid state onto the fluid bag 101, after which the coating similarly dries, forming a protective layer.

II. Cartridge and Blood Analysis Machine

Figure 2A:
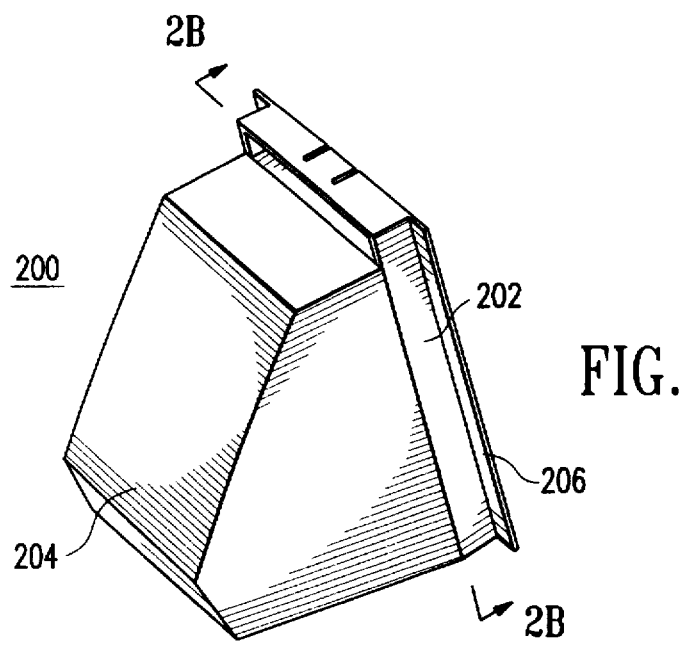
FIG. 2A is a perspective view of a container cartridge for holding the reference solution container of the present invention.

FIG. 2A shows a cartridge 200 that can be employed to hold one or more reference solution containers 100. The cartridge 200 may have a tray 202 and cover 204 that are secured together to enclose the containers 100. The cartridge illustrated in FIG. 2 is merely exemplary. It should be recognized that the cartridge 200 may have almost any shape and need not completely enclose the containers 100. The cartridge may have at least one rail 206 for aligning the cartridge 200 with a housing for a blood analysis device, as will be described with reference to FIG. 3. The cartridge 200 may be made from plastic or any other suitable material. A more detailed description of an exemplary cartridge can be found in a U.S. patent application Ser. No. 08/650,340, filed May 20, 1996, entitled "Integral Fluid and Waste Container for Blood Analyzer," assigned to the assignee of the present application and referenced above.

Figure 2B:
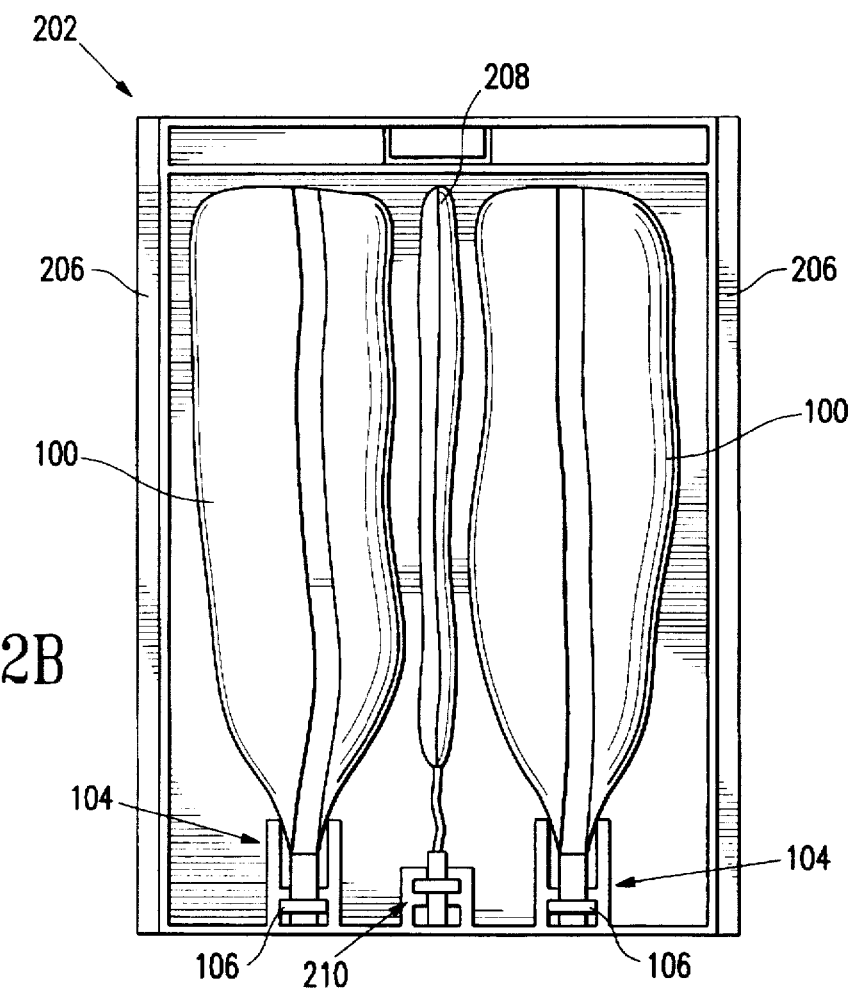
FIG. 2B is a cut-away view of the container cartridge of FIG. 2A along line 2B—2B.

FIG. 2B is a cut-away view of the cartridge 200 along line 2B—2B of FIG. 2A. This view shows the tray 202 holding two reference solution containers 100 and a waste bag 208. The waste bag 208 collects waste fluids (such as blood and used reference solution) from the blood analysis device. The waste bag 208 has a waste fluid port 210, which is preferably a one-way valve that only permits waste fluids (and gases) to enter the waste bag 208. The reference solution containers 100, being preferably flexible, contract as reference solution exits the containers 100. As the containers 100 contract, they leave a void in the cartridge 200. This void may be filled by the waste bag 208 as it expands with waste fluid. Preferably, the waste bag 208 may contain a moisture absorbent material that converts the incoming waste fluid into a substantially solid material. A more detailed description of a waste bag can be found in a U.S. patent application Ser. No. 08/650,624, filed May 20, 1996, entitled "Waste Container for Portable Blood Analyzer," assigned to the assignee of the present application and referenced above.

Figure 3:
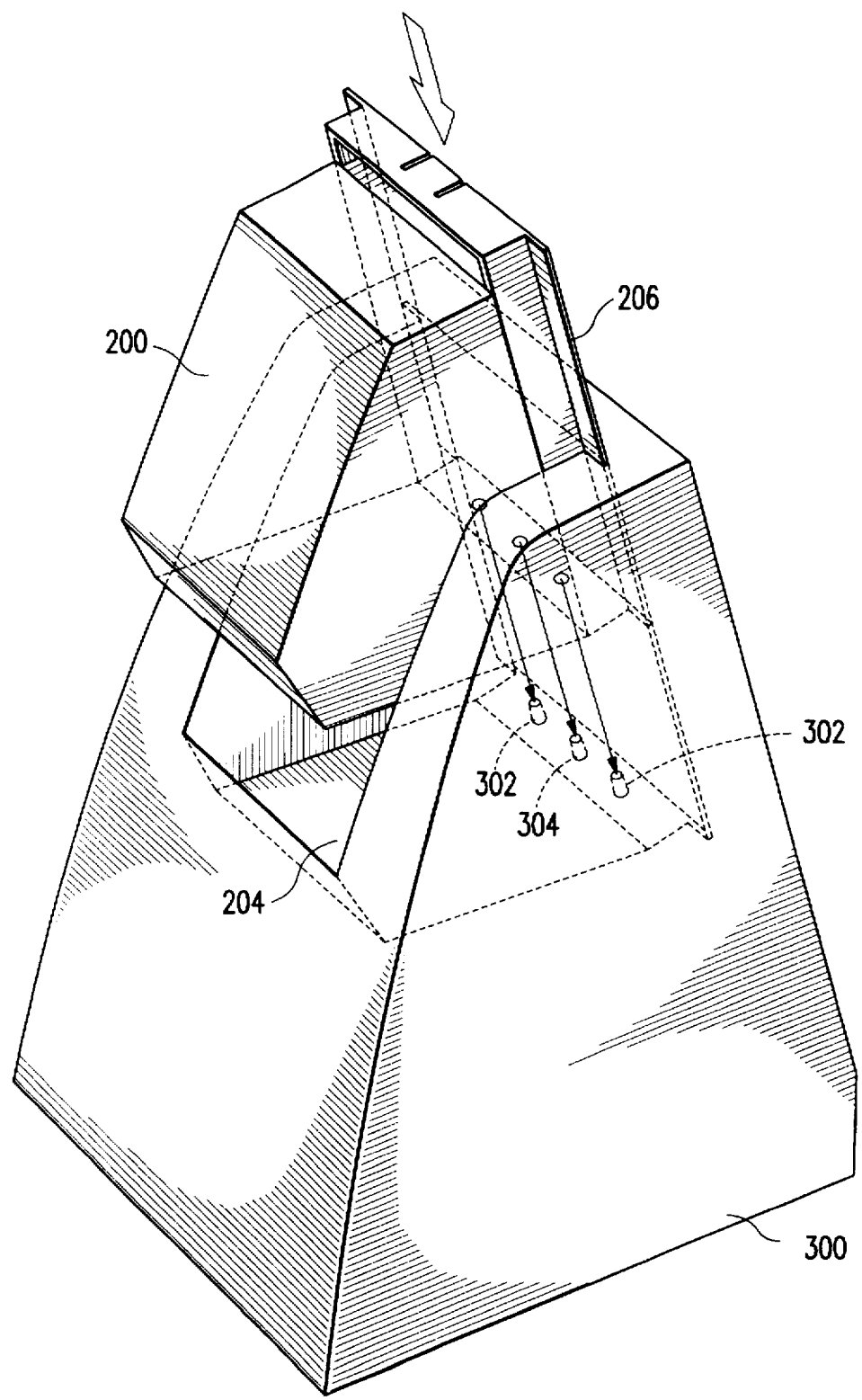
FIG. 3 shows the cartridge of FIG. 2 secured within a blood analysis device.

FIG. 3 shows the housing of a blood analyzer 300 with the cartridge 200 inserted into a cavity in the blood analyzer 300. The rails help guide the cartridge 200 into the blood analyzer 300, such that the fluid port 104, 210 for the reference solution bags 100 and waste bag 208 will properly engage fluid carrying devices (or fittings) 302, 304 that are part of the blood analyzer 300. Fluid fittings 302 are positioned on the blood analyzer 300 to engage the fluid ports 104 on the reference solution bags 100, and fluid fitting 304 is positioned to engage the fluid port 210 on the waste bag 208. The fluid fittings 302, 304 protrude from and are part of the blood analyzer 300. As such, the fittings 302, 304 constitute fluid carrying devices that are external to the reference solution containers 100 and the waste bag 208. A more detailed description of an exemplary blood analyzer can be found in a U.S. patent application Ser. No. 08/650,341, entitled "Portable Modular Blood Analyzer with Simplified Fluid Handling Sequence," filed May 20, 1996, assigned to the assignee of the present application, and referenced above.

III. Self-Sealing Fluid Port

FIGS. 4A–4F illustrate an exemplary embodiment of the self-sealing fluid port 104. Because the reference solution container 100 can be used for calibrating devices used to measure gases in fluids, such as blood, the self-sealing fluid port 104 is preferably substantially gas-tight. The substantially gas-tight seal helps to maintain the partial pressure of the gases (such as oxygen and carbon dioxide) in solution within the container 100. The self-sealing feature of the fluid port 104 helps attain a gas-tight seal, because each time the external fluid carrying device 302 is disengaged from the fluid port 104, the fluid port automatically reseals. The fluid port 104 is also preferably directly coupled (without external plastic tubing, or the like) to the external fluid carrying device 302 to help prevent any appreciable loss of gases in the reference solution through external plastic tubing, gas-permeable fitting, and the like, connecting the fluid port 104 to an external fluid carrying device.

In the preferred embodiment of the reference solution container 100, the self-sealing fluid port 104 is a two-way valve. When engaged by an external fluid carrying device, the container 100 can be filled with reference solution via the fluid port 104. Additional reference fluid or other ingredients can also be added to the container 100 via the fluid port 104 after the initial filling. Then, when the container 100 is filled, the solution within the container 100 can be accessed by an external fluid carrying device to drain the container 100 and calibrate a fluid analysis device.

Figure 4A:
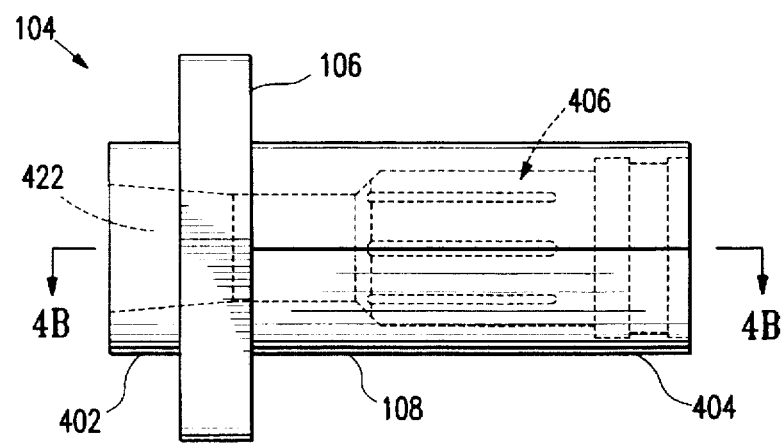
FIG. 4A is a side-view of an exemplary self-sealing fluid port coupled to a fluid vessel of the present invention.

FIG. 4A is a side-view of the preferred self-sealing fluid port 104 of the present invention. The fluid port 104 has a port body 108, a flange 106, a fitting end 402, a bag end 404, a fluid communication path 422, and a self-sealing valve assembly 406. The self-sealing valve assembly 406 is located within the fluid communication path 422, which is coaxial with the port body 108. The flange 106 substantially surrounds the port body 108, the two elements preferably being an integral assembly formed from polypropylene. Those skilled in the art will recognize that, while polypropylene is the preferred material, other suitable materials exist.

Figure 4B:
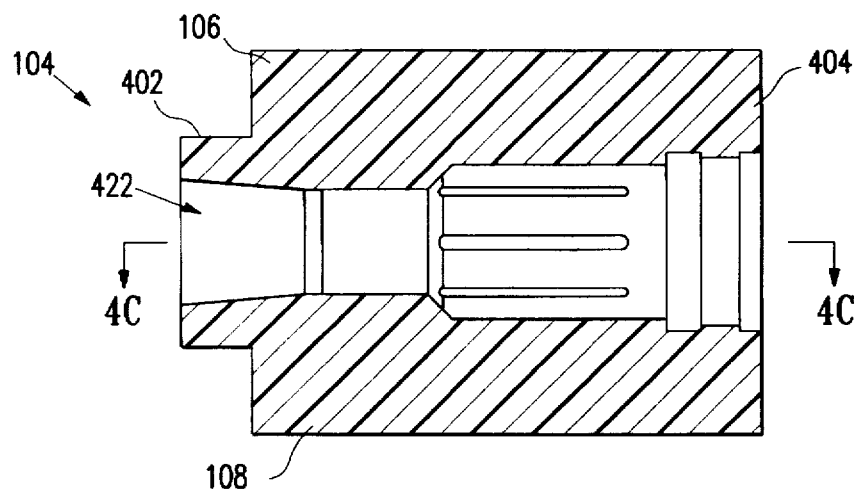
FIG. 4B is a cut-away view of the self-sealing fluid port along line 4B—4B.

FIG. 4B is a cut-away view of the self-sealing fluid port 104 along line 4B—4B in FIG. 4A. The view of FIG. 4B shows that the bag end 404 is asymmetrical in shape, as it is wider in one cross section (FIG. 4B) than in the other (FIG. 4A). Preferably, if the reference solution container 100 is a bag made from a flexible aluminum material, the bag end 404 is substantially elliptical in shape, for thermally-sealing the bag 100 to the fluid port 104. An elliptical shape facilitates a stronger thermal seal between the bag 100 and the port 104. If thermally sealed, the material from which the fluid port 104 is made should be compatible with the melting characteristics of the material (e.g., aluminum-plastic laminate) forming the bag 100. Alternatively, the fluid port 104 and the bag 100 can be adhesively coupled to one another. FIG. 4B also shows that, from this view, the flange 106 and the bag end 404 have the same dimensions.

Figure 4C:
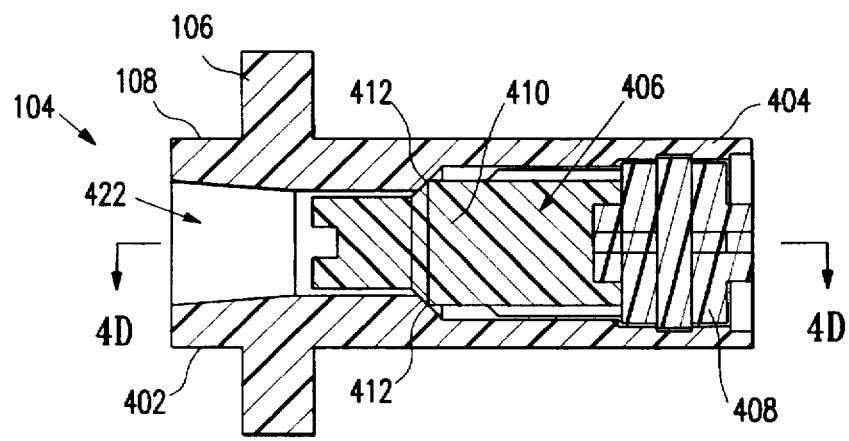
FIG. 4C is a cut-away view of the self-sealing fluid port along line 4C—4C, showing a self-sealing valve assembly within the port.

FIG. 4C is a cut-away view of the self-sealing fluid port 104 along line 4C—4C in FIG. 4B showing the self-sealing valve assembly 406. The assembly is preferably a poppet valve, including a stem backstop 408 and a stem 410, the latter preferably being made of silicone. When a fluid fitting 302 (preferably a Luer fitting) is inserted into the fluid communication path 422, the fitting 302 engages the silicon stem 410 (which is compressible), forcing the stem 410 back against the stem backstop 408, which is secured in place within the fluid communication path 422 of the port body 108. The silicon stem 410 is thus pushed rightward (with reference to FIG. 4C) until a gap forms between the stem 410 and bevels 412. This creates an opening through the fluid communication path 422 to the stem backstop 408, which has channels through which fluid can flow, thereby allowing fluid flow through the self-sealing fluid port 104 and out of the reference solution container 100.

When the external fluid carrying device 302 is removed from the fluid communication path 422 of the self-sealing fluid port 104, the resilient silicon stem 410 expands leftward (with reference to FIG. 4C), resealing the gap between the stem 410 and the bevels 412, thereby preventing further fluid flow through the fluid communication path 422. Thus, in the preferred embodiment, the fluid port 104 is self-sealing, so that, when the external fluid carrying device 302 is removed from the fluid port 104, no appreciable amount of fluid will exit the reference solution bag 100.

Figure 4D:
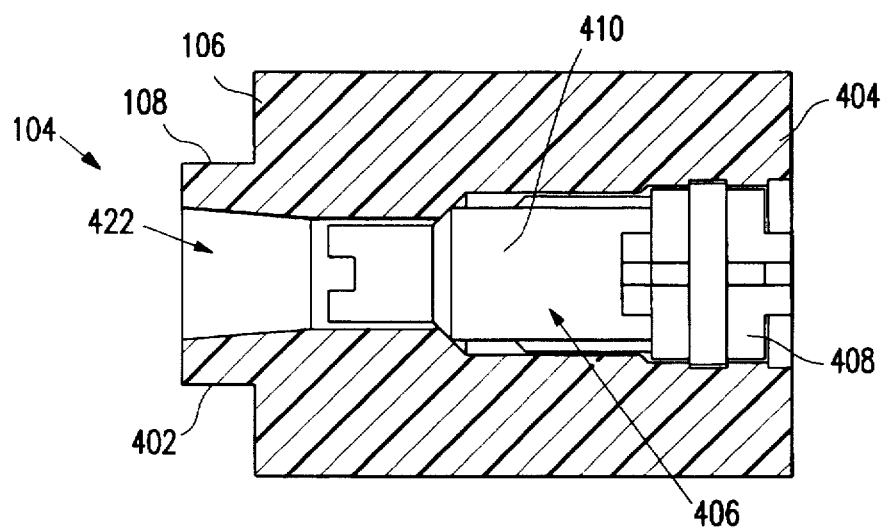
FIG. 4D is a top cut-away view of the self-sealing fluid port along line 4B—4B, showing the self-sealing valve assembly and an elliptical shape on the end of the port that engages the fluid vessel.
Figure 4E:
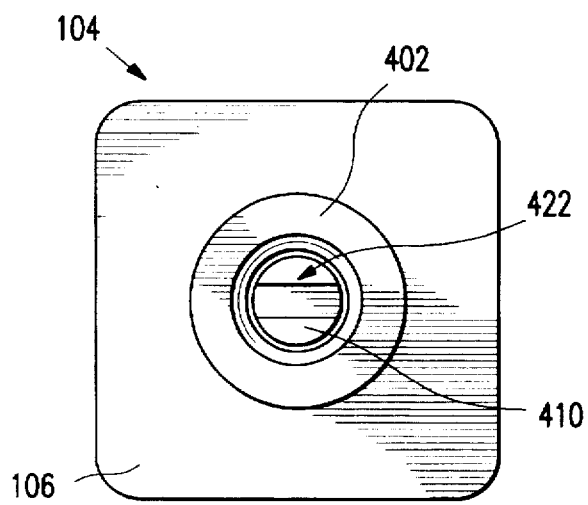
FIG. 4E is a front view of the self-sealing fluid port, showing a flange on the port.
Figure 4F:
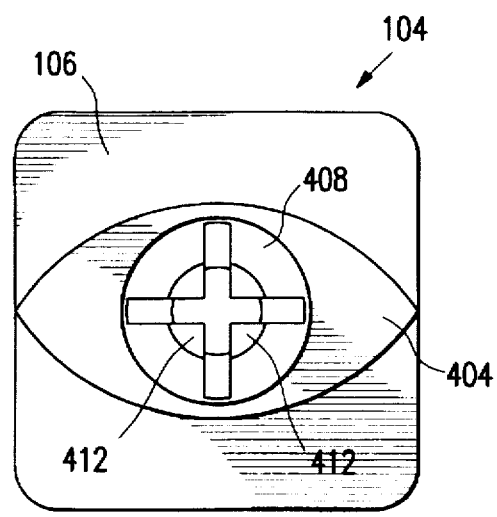
FIG. 4F is a rear view of the self-sealing fluid port.

FIG. 4D is a top cut-away view of the fluid port 104 along line 4D—4D in FIG. 4C showing the self-sealing valve 406 with respect to the preferred elliptical bag end 404. FIG. 4E is a front view of the fluid port 104 showing that the flange 106 is preferably rectangular in shape and showing the front of the valve stem 410 within the fluid communication path 422. FIG. 4F is a rear view of the fluid port 104, showing the elliptical shape of the bag end 404 and the rear of the stem backstop 408 within the fluid communication path 422. As can be seen, the stem backstop 408 has spaces (or channels) 412 through which fluid can flow.

IV. Characteristics of the Reference Solution Container

The reference solution container 100 of the present invention maintains a substantially constant partial pressure level of each gas in solution within the container 100 for substantially the life of the container 100. The reference solution within the container 100 contains at least one gas having a partial pressure. For example, the reference solution may contain oxygen and carbon dioxide gases as well as other gases. It is important to maintain the partial pressure of each gas in solution, because, if the partial pressures are not maintained at a substantially constant level, the reference solution cannot be used to calibrate the blood analysis device 300; the solution will inaccurately recalibrate.

Tests have been run with the container 100 of the present invention to demonstrate that the partial pressure of the gases in the container 100 remain substantially constant for a sufficient duration to give the container 100 a reasonable shelf life and a reasonable lifespan when in use on the blood analysis device 300. In the first test, a preferred composition of Reference Solution I, prepared at 37 degrees Celsius and at atmospheric pressure tonometered with 5% $CO_2$, 20% $O_2$, and the balance of $N_2$, is as follows:

TABLE 1

| Compound | Concentration |
| --- | --- |
| Buffer, 3-Morpholinopropane-Sulfonic Acid (MOPS) | 4.1 mmol/liter |
| Buffer, NaMOPS | 12.6 mmol/liter |
| KCl | 3.5 mmol/liter |
| NaCl | 108 mmol/liter |
| $NaC_2H_3O_2$ | 10 mmol/liter |
| $NaHCO_3$ | 20 mmol/liter |
| $CaCl_2$ | 1.6 mmol/liter |
| Glutaraldehyde (25% wt./vol.) | 0.63 ml/liter |
| Water | 1.0 liter |

The reference compositions were prepared by premixing all of the constituents, followed by tonometering the solution at 37 degrees Celsius and ambient atmospheric pressure with oxygen and $CO_2$ mixed with nitrogen to produce the desired level of $pCO_2$, $pO_2$, and pH for the solution. The resulting solution was transferred substantially gas-tightly into substantially evacuated foil fluid bags 101 through the self-sealing fluid port 104 of the present invention. The resulting packages contain Reference Solution I showing a pH of approximately 7.4, $pCO_2$ of approximately 33 mmHg, and $pO_2$ of approximately 145 mmHg and are suitable for blood-gas calibrating/control solutions. Electrolytes used in this solution have the approximate measured values, $K^+$ 3.3 mM/liter, $Na^+$ 144 mM/liter, $Ca^{++}$ 1.35 mM/liter, and $Cl^-$ 110 mM/liter, which can be used for calibration/control of the corresponding electrolyte sensor in the blood analyzer 300.

In the second test, a preferred composition of Reference Solution II, prepared at 37 degrees Celsius and at atmospheric pressure tonometered with 10% $CO_2$, 20% $O_2$, balance $N_2$ gas, is as follows:

TABLE 2

| Compound | Concentration |
| --- | --- |
| Buffer, 3-Morpholinopropane-Sulfonic Acid (MOPS) | 14.1 mmol/liter |
| Buffer, NaMOPS | 12.6 mmol/liter |
| KCl | 8.9 mmol/liter |
| NaCl | 86 mmol/liter |
| $NaC_2H_3O_2$ | 10 mmol/liter |
| $NaHCO_3$ | 20 mmol/liter |
| $CaCl_2$ | 4.9 mmol/liter |
| Glutaraldehyde (25%) | 0.63 mmol/liter |
| Water | 1.0 liter |

When Reference Solution II was prepared in a similar manner to Reference Solution I (described above), the resulting packages contain reference solution showing a pH of approximately 7.0, $pCO_2$ of approximately 65 mmHg, and $pO_2$ of approximately 150 mmHg. Electrolytes used in this solution have the approximate measured values: $K^+$ 8.7 mM/liter, $Na^+$ 122 mM/liter, $Ca^{++}$ 4.1 mM/liter, and $Cl^-$ 99 mM/liter.

The stability of reference solutions packaged in the manner described above for Reference Solutions I and II is shown in Table 3 below. In these examples, 14 packages each from Lot A and Lot B were repeatedly tested using two blood gas analysis instruments. Overall average values and standard deviations were calculated for $O_2$ and $CO_2$ at the sampling times indicated.

TABLE 3

| Time (days) | $CO_2$ mmHg | Standard Dev. (S.D.) | $O_2$ mmHg | S.D. |
| --- | --- | --- | --- | --- |
| LOT A | | | | |
| 0 | 32.9 | 0.4 | 148.6 | 1.5 |
| 49 | 32.5 | 0.3 | 145.0 | 1.2 |
| 80 | 32.4 | 0.2 | 145.9 | 1.6 |
| 97 | 32.3 | 0.3 | 146.5 | 1.1 |
| LOT B | | | | |
| 0 | 32.7 | 0.6 | 147.2 | 1.2 |
| 57 | 32.2 | 0.4 | 144.8 | 1.6 |
| 75 | 32.2 | 0.4 | 145.7 | 1.7 |
| 92 | 32.0 | 0.5 | 145.4 | 2.2 |

It is believed that compositions of Reference Solutions I and II can be tonometered at temperatures other than 37 degrees Celsius and with gas concentrations other than 10% or 5% $CO_2$ and 20% $O_2$, the balance $N_2$.

To increase shelf life of reference solutions packaged in the reference solution container 100, or if necessary to have gas concentrations varying widely from ambient, the self-sealing fluid port (or valve) 104 on a reference solution container 100 may be covered with an aluminum (or foil) material 502. The foil tape 502 protects the valve 104 and further prevents the communication of gas through the valve 104 during transport and storage of the container 100. A metallized tape such as 3M No. 425 aluminum foil tape over the valve 104 results in improved stability of the reference solution within the container 100. Table 4 shows test results for reference solutions Lot C, containing $pCO_2$ of 63 mmHg packaged without foil tape 502, and Lot D, containing $pCO_2$ of 66.2 mmHg packaged with foil tape 502.

TABLE 4

| Time (days) | $CO_2$ mmHg | S.D. |
| --- | --- | --- |
| LOT C | | |
| 0 | 63 | 0.4 |
| 72 | 57 | 0.5 |
| LOT D | | |
| 0 | 66.2 | 0.6 |
| 63 | 66.6 | 0.6 |

As can be seen in Table 4, Lot D, which was equipped with foil tape 502, remains more stable for a longer period of time than Lot C, which did not include foil tape 502.

Figure 5:
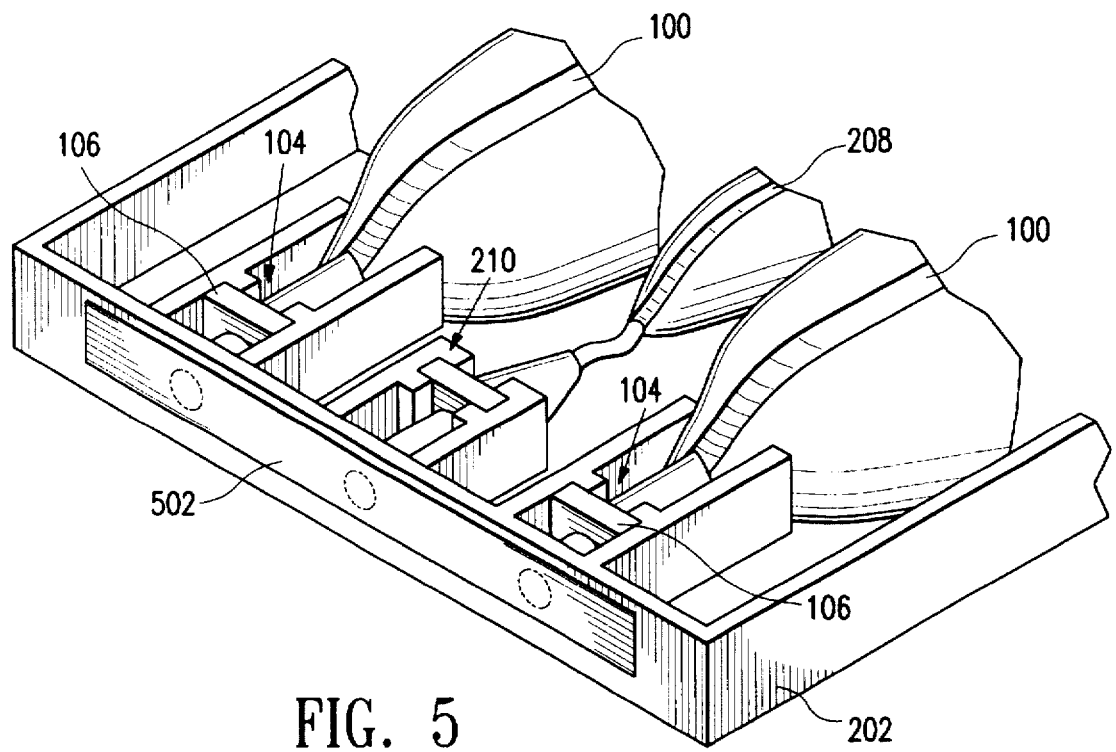
FIG. 5 shows a foil tape secured to the self-sealing fluid ports of two reference solution containers and a waste container.

FIG. 5 shows tray 202 with foil tape 502 covering the self-sealing fluid ports (or valves) 104 and waste fluid port 210. It should be understood, however, that the foil tape 502 need not be a single piece, like that shown in FIG. 5, but instead could be independent pieces covering each port from which it is desirable to protect against the escape of gases and to prevent dirt from interfering with the valves 104, 210. When the cartridge 200 is ready to be inserted into the blood analyzer 300, the foil tape 502 is preferably first removed, although the cartridge 200 can be inserted into the analyzer 300 with the foil 502 in place, and the fittings 302, 304 would then puncture the foil tape 502 when inserted into the valves 104, 210. Those skilled in the art will recognize that the foil tape 502 is merely an exemplary means by which the self-sealing valves 104, 210 can be further sealed against the escape or ingress of gases. Other means include metal or plastic plugs or caps.

With the foil tape 502 in place, the reference solution containers 100 are even further substantially sealed against the communication of gases through the valve 104.

A reference solution container 100 may be filled with reference solution to an internal pressure greater than ambient. By over-filling the reference solution container 100 with reference solution, the container 100 can hold more reference solution than conventional containers, which are filled to an internal pressure less than or equal to the ambient atmospheric pressure. The ability to hold more reference solution means the over-filled reference solution container 100 lasts longer and need not be replaced as often as a conventional bag. This results in more blood tests per container 100.

Over-filling the reference solution container 100 also reduces the susceptibility to barometric pressure changes of the gases in solution within the over-filled container 100. Thus, the tonometry level of those gases is maintained at a substantially constant level.

It is believed that the structural relationship of the reference solution containers 100, the waste bag 208, and the cartridge 200 help maintain the tonometered state of the oxygen gas and maintain the pressure level within the sealed containers 100 for substantially all of their lifetime, even when changes occur in the barometric pressure surrounding the containers 100. The containers 100, when full of reference solution, and the empty waste bag 208, preferably fit relatively snugly within the cartridge 200. Thus, during transport and storage (e.g., when the cartridge 200 has not been used), the reference solution containers 100 are constrained by the walls of the cartridge 200. As the containers 100 are emptied during blood tests, the void they leave within the cartridge 200 from their decreasing internal volume is filled by the expanding waste bag 208, which holds the waste blood and waste reference solution from the blood analyzer 300. Accordingly, the reference solution containers 100 remain constrained, now by the walls of the cartridge 200 and the expanding waste bag 208, as the reference solution containers 100 are emptied of reference solution.

Further, a relatively small amount of head space (e.g., air) may be maintained within the reference solution bags 100. Because the fluid bag portion 101 of the containers 100 is preferably made from an aluminum-plastic laminate material, some oxidation may occur within the fluid bag 101, thereby reducing the amount of oxygen gas in solution within the fluid bag 101. Oxygen gas in the head space may replenish the oxygen gas lost from the reference solution. The amount of head space within the fluid bag 101 is no more than about 5% of the overall internal volume of the bags 101 and is preferably in the range of about 0.01% to about 0.1% of the internal volume.

It has been experimentally observed that the reference solution containers 100 of the present invention maintain the internal tonometered gases at substantially the same partial pressure levels for most of the lifetime of the containers 100. Even when the assembly of the cartridge 200, reference solution containers 100, and waste bag 208 experiences varying external barometric pressures, it has been observed that the substantially constant partial pressures are maintained at least until the containers 100 are substantially drained of the reference solution. Maintenance of gas levels within the reference solution containers 100 is important to attain accurate calibration of blood-gas analyzers 300.

The reference solution containers 100 can be filled with reference solution according to a particular method involving several steps. First, a vacuum is applied to an empty reference solution container 100, evacuating the interior of the fluid bag 101. This is conventionally done with a vacuum pump, which is preferably coupled to the fluid bag 101 via the self-sealing fluid port (or valve) 104. Second, the vacuum pump is removed from the valve 104. Because the valve 104 is self-sealing (as described above), when the vacuum pump is removed from the valve 104, the fluid bag 101 remains reasonably sealed. Third, a fluid fitting is inserted into and unseals the valve 104, and the fluid bag 101 is filled with reference solution. Finally, the fluid bag 101 is "burped" or "expressed" to remove excess gases within the bag 101.

A manifold can be used to alternately couple the reference solution container 100 to the vacuum pump and the source of the reference solution. If such a manifold is used, the first and third steps can be performed without the second step.

IV. Multi-Layered Laminates for Improved Oxygen Partial Pressure Retention

The fluid bag 101 of the present invention is preferably formed from a multi-layered laminate. It should be understood, however, that lamination is not the only way that the multi-layered structure can be formed. Alternatively, the structure could be co-extruded or processed by vapor deposition. For simplicity, we will limit our description to laminated multi-layer structures.

Two sheets of the laminate are preferably constructed and are secured together to form the fluid bag 101. The laminate fluid bag 101 may also be equipped with the self-sealing port 104 of the present invention, or any other suitable fluid port. Depending on the materials forming the layers, they may be heat-sealed together.

Figure 6:
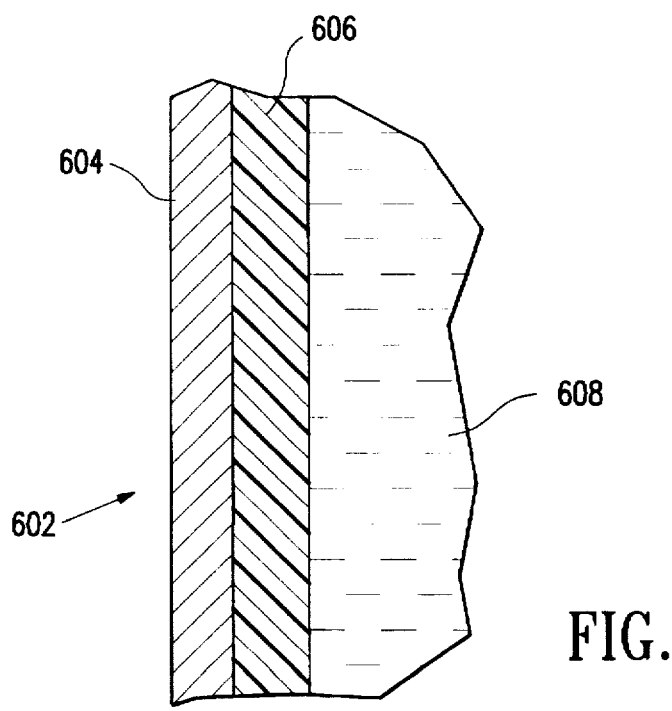
FIG. 6 is a cross-section of a two-layered material used to form the walls of a fluid vessel.

FIG. 6 shows a multi-layer laminate 602 having at least two layers: an external metallic layer 604 and an internal sealing layer 606. The sealing layer 606 forms a barrier between the reference solution 608 contained in the fluid bag 101 and the metallic layer 604. Preferably, the sealing layer 606 covers substantially all of the interior of the fluid bag 101, such that no portion of the metallic layer 604 is exposed to the reference solution 608. The sealing layer 606 thereby substantially prevents decreases in the partial pressure level of oxygen gas held in the reference solution 608 due to interaction with the metallic layer 604.

Preferably, the sealing layer 606 is polypropylene. The use of polypropylene provides a significant improvement over the performance of polyethylene-lined fluid bags 101. Over time, the partial pressure level of oxygen gas in the reference solution will decrease at a significantly slower rate than it would if polyethylene were used. Consequently, the laminate bags of the present invention provide a significant improvement in shelf-life and use-life of the reference fluid containers 100 of the present invention.

The following experiments were conducted to demonstrate the improved performance resulting from the use of polypropylene-lined versus polyethylene-lined fluid bags. In the first experiment, the following composition shown in TABLE 5 was prepared for the reference solution at 37 degrees Celsius and at atmospheric pressure tonometered with 5% carbon-dioxide gas, 20% oxygen gas, and the balance of nitrogen gas:

TABLE 5

| Compound | Concentration |
| --- | --- |
| Potassium Chloride | 0.261 grams/Liter |
| Sodium Chloride | 6.271 g/L |
| Sodium Sulfate | 0.71 g/L |
| Sodium Bicarbonate | 1.680 g/L |
| Buffer, 3-Morpholinoporpane Sulfonic Acid (MOPS) | 0.853 g/L |
| Buffer, Na MOPS | 2.913 g/L |
| Calcium Chloride | 0.178 g/L |
| Glutaraldehyde (25% wt/vol) | 0.63 ml/L |
| Water | 1.0 liter |

The resulting solution was transferred substantially gas-tightly into substantially evacuated foil fluid bags ("Material I") through a self-sealing fluid port 104 of the present invention. The Material I bags were lined on their interior with polypropylene. The resulting reference solution containers ("Lot 1") contain a solution showing a $PO_2$ of approximately 147 mmHg. In this experiment, Lot 1 included four bags that were allowed to cool to room temperature before the initial sampling. The $pO_2$ levels indicated in TABLE 6 below are the average of samples from each bag at the indicated time period ran on each of two Radiometer ABL330 Blood Gas and pH instruments. Aging of the bags was conducted at room temperature.

In a similar experiment, buffer solution was prepared and tonometered at 23 degrees Celsius. This solution was transferred substantially gas-tightly into six different foil containers ("Material II") having an interior lining of polyethylene. The resulting reference solution containers, numbered A–F, contain a solution showing a $pO_2$ of approximately 181 mmHg.

Containers A–C were sampled at a reference point (0 days), and containers D–F were sampled 21 days after the reference day. Results when aged at room temperature for 21 days are shown below in TABLE 6.

TABLE 6

Material I: Polypropylene Lined Reference Solution Containers

| Container Lot | Time (days) | $pO_2$ (mmHg) |
| --- | --- | --- |
| Lot 1 | 0 | 147 |
| Lot 1 | 13 | 147 |
| Lot 1 | 57 | 145 |
| Lot 1 | 75 | 146 |
| Lot 1 | 92 | 145 |

Material II: Polyethylene Lined Reference Solution Containers

| Container Number | Time (days) | $pO_2$ (mmHg) |
| --- | --- | --- |
| Container A | 0 | 181 |
| Container B | 0 | 179 |
| Container C | 0 | 180 |
| Container D | 21 | 129 |
| Container E | 21 | 157 |
| Container F | 21 | 137 |

The results of the experiments shown in TABLE 6 demonstrate that the polypropylene-lined reference solution containers maintain the partial pressure of oxygen gas substantially better than do polyethylene-lined containers.

Extrapolating the data included in TABLE 6 for the polypropylene-lined fluid bag, it is believed that such fluid bag would have a shelf-life of at least about 12 months and a use-life of at least about 3 months. It is possible, however, that the polypropylene-lined fluid bags of the present invention could have a longer shelf-life and/or use-life.

FIGS. 7A–7C show three alternative embodiments 700, 720, 740, respectively, for multi-layered structures forming a fluid bag. Preferably, the layers in each embodiment are laminated together. An adhesive may also be applied between the layers. Those skilled in the art will recognize, however, that lamination is not the only means by which the layers can be secured together. Other means include co-extrusion and vapor deposition of one or more layers.

The embodiment 700 illustrated in FIG. 7A has four layers. The inside sealing layer 702, which is in contact with the reference solution, is made from polypropylene having a thickness of approximately $3/1000$ of an inch. Next, is an aluminum foil layer 704, adhered to the sealing layer 702, and having a thickness of about $0.7/1000$ of an inch. In this embodiment, the foil layer 704 is a foil produced by Kapak Corp. Adhered to the foil layer 704 is a white ink layer 706. Finally, the exterior layer 708 of wall 700 is made from a 50 gauge PET material.

FIG. 7B shows a second embodiment 720 having five layers. The inside sealing layer 722 is again 3 mil polypropylene, which is adhered to a first foil layer 724 having a thickness of about $0.35/1000$ of an inch. This foil layer 724 is preferably made from a foil sheet produced and sold by Technipaq, Inc. The first foil layer 724 is then adhered to a first 48 gauge PET layer 726. A second Technipaq foil layer 728 having a thickness of $0.35/1000$ of an inch is then sandwiched between the first 48 gauge PET layer 726 and a second identical layer 730, which constitutes the exterior layer of the wall 720.

FIG. 7C shows a third embodiment 740, also having five layers. The five layers of this wall 740, in order from interior to exterior surface are as follows: (1) a 3 mil polypropylene layer 742, (2) a first 48 gauge PET layer 744, (3) a first $0.35/1000$ inch Technipaq foil layer 746, (3) a second identical foil layer 748, and (5) a second 48 gauge PET layer 750.

Preferably, the polypropylene sealing layer has a thickness in a range of about $1.5/1000$ of an inch and about $10/1000$ of an inch. The 3 mil layer was chosen for the embodiments 700, 720, and 740 because sheets of this thickness polypropylene are widely used commercially and are available at reasonable pricing. The thinner the polypropylene sealing layer, the less effective barrier it provides between the reference solution and the metallic layer (e.g., the foil layer). If the polypropylene layer is too thick, the fluid bag will be relatively inflexible, an undesirable result.

It should be recognized that alternative materials besides polypropylene exist that could be used as a barrier layer in the present invention. For example, flexible glass can be deposited on a substrate layer, such as an aluminum foil layer. The deposited glass would provide a substantially gas impermeable barrier between the substrate layer and the reference solution. A glass barrier, therefore, would substantially maintain the partial pressure of oxygen gas in the reference solution. Other suitable materials for the sealing layer include Barex and Saran, which are both commercially available.

Several embodiments of the present invention have been described. Nevertheless, it will be understood that various modifications may be made without departing from the spirit and scope of the invention. For example, the reference solution container 100 of the present invention can have a protective layer applied to external surface of the container 100 for added protection against bursting and puncturing.

Furthermore, the reference solution container 100 may be filled to an internal pressure that is greater than the ambient atmospheric pressure. Accordingly, it is to be understood that the invention is not to be limited by the specific illustrated embodiment, but only by the scope of the appended claims.

What is claimed is:

1. A reference solution container with improved oxygen gas partial pressure retention, the reference solution container for holding a reference solution in an analyzer for measuring gas levels in a fluid, the reference solution container having an interior surface, comprising:

a. a polypropylene sealing layer forming substantially all the interior surface of the reference solution container, the polypropylene sealing layer being in contact with the reference solution and b. a substrate layer secured to the polypropylene sealing layer.

2. The reference solution container of claim 1 wherein the reference solution has an initial $O_2$ gas partial pressure level when the reference solution is first introduced into the reference solution container, and the presence of the polypropylene sealing the layer reduces a rate of decrease of the $O_2$ gas partial pressure from the initial level relative to a rate of decrease that occurs when the sealing layer is formed from polyethylene.

3. The reference solution container of claim 1 wherein the polypropylene sealing layer has a thickness in a range between about 1.5/1000 of an inch and about 10/1000 of an inch.

4. The reference solution container of claim 3 wherein the thickness of the polypropylene sealing layer is about 3/1000 of an inch.

5. The reference solution container of claim 1 wherein the substrate layer is formed from a metallic material, and the polypropylene sealing layer forms a barrier between the metallic substrate layer and the reference solution to retard reduction of oxygen in the reference solution.

6. The reference solution container of claim 1, further comprising a fluid port for communicating fluid between the interior of the reference solution container and an external environment.

7. The reference solution container of claim 6 wherein the container has a shelf life and a use life; and wherein the shelf life is at least about 8 months and the use life is at least about 3 weeks.

8. The reference solution container of claim 1 wherein the reference solution has an $O_2$ gas partial pressure level; and wherein the $O_2$ gas partial pressure level decreases at a slower rate with the polypropylene sealing layer than if the sealing layer is formed from polyethylene.

9. The reference solution container of claim 1 wherein the reference solution container has a shelf life of at least 12 months and a use life of at least 3 months.

10. A reference solution container for holding a reference solution in an analyzer for measuring gas levels in blood, the reference solution containing $O_2$ gas at a partial pressure level and the reference solution container having an interior surface, comprising:

a. a metallic substrate layer; and b. a polypropylene sealing layer, bonded to the metallic substrate layer to form substantially all the interior surface of the reference solution container and being in contact with the reference solution, for forming a barrier between the reference solution and the metallic substrate to substantially prevent a decrease in the $O_2$ gas partial pressure level due to interaction of the reference solution with the metallic substrate layer.

11. The reference solution container of claim 10 wherein the metallic substrate layer is formed from an aluminum foil material and is laminated to the polypropylene sealing layer.

12. The reference solution container of claim 10 wherein the polypropylene sealing layer has a thickness of between about 1.5/1000 of an inch and about 10/1000 of an inch.

* * * * *